(12) United States Patent
Defossa et al.

(10) Patent No.: US 7,179,941 B2
(45) Date of Patent: Feb. 20, 2007

(54) CARBONYLAMINO-SUBSTITUTED ACYL PHENYL UREA DERIVATIVES, PROCESS FOR THEIR PREPARATION AND THEIR USE

(75) Inventors: Elisabeth Defossa, Idstein (DE); Dieter Kadereit, Kelkheim (DE); Thomas Klabunde, Frankfurt (DE); Hans-Joerg Burger, Morristown, NJ (US); Andreas Herling, Bad Camberg (DE); Karl-Ulrich Wendt, Frankfurt (DE); Erich Von Roedern, Hattersheim (DE); Karl Schoenafinger, Alzenau (DE); Alfons Enhsen, Büttelborn (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 400 days.

(21) Appl. No.: 10/763,877

(22) Filed: Jan. 23, 2004

(65) Prior Publication Data

US 2005/0014822 A1    Jan. 20, 2005

Related U.S. Application Data

(60) Provisional application No. 60/478,757, filed on Jun. 16, 2003.

(30) Foreign Application Priority Data

Jan. 23, 2003  (DE)  ............................ 103 02 452
Jan. 7, 2004   (WO)  ...................... PCT/EP04/00041

(51) Int. Cl.
*C07C 273/00* (2006.01)
*C07C 53/00* (2006.01)
*C07C 59/00* (2006.01)
*C07C 229/00* (2006.01)
*A61K 31/00* (2006.01)

(52) U.S. Cl. .................. 564/44; 562/512; 562/579; 560/19; 514/331; 514/461; 514/532; 514/571; 514/594

(58) Field of Classification Search .............. None
See application file for complete search history.

(56) References Cited

U.S. PATENT DOCUMENTS

| | | | |
|---|---|---|---|
| 5,190,923 | A | 3/1993 | Vincent et al. |
| 6,221,633 | B1 | 4/2001 | Ertl et al. |
| 6,221,897 | B1 | 4/2001 | Frick et al. |
| 6,245,744 | B1 | 6/2001 | Frick et al. |
| 6,342,512 | B1 | 1/2002 | Kirsch et al. |
| 6,441,022 | B1 | 8/2002 | Frick et al. |
| 6,506,778 | B2 | 1/2003 | Defossa et al. |
| 6,566,340 | B2 | 5/2003 | Frick et al. |
| 6,569,835 | B2 | 5/2003 | Frick et al. |
| 6,624,185 | B2 | 9/2003 | Glombik et al. |
| 6,642,269 | B2 | 11/2003 | Frick et al. |
| 6,884,812 | B2 | 4/2005 | Glombik et al. |
| 6,897,198 | B2 | 5/2005 | Frick et al. |

FOREIGN PATENT DOCUMENTS

| | | |
|---|---|---|
| EP | 0749751 | 12/1996 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 99/46236 | 9/1999 |
| WO | WO 00/07991 | 2/2000 |
| WO | WO 00/40569 | 7/2000 |
| WO | WO 00/45818 | 8/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/83451 | 11/2001 |
| WO | WO 01/85695 | 11/2001 |
| WO | WP 01/91752 | 12/2001 |
| WO | WO 03/104188 | 12/2003 |

OTHER PUBLICATIONS

Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.

Drueckes P et al., Photometric Microtiter Assay of Inorganic Phosphate in the Presence of Acid-Labile Organic Phosphates, Anal. Biochem. 1995, vol. 230(1), pp. 173-177.

Engers H D et al., Kinetic mechanism of phosphorylase a. 1. Initial velocity studies, Can. J. Biochem., 1970, vol. 48(7) pp. 746-754.

(Continued)

*Primary Examiner*—Sikarl A. Witherspoon
(74) *Attorney, Agent, or Firm*—Barbara E. Kurys

(57) ABSTRACT

The invention relates to compounds of the formula I

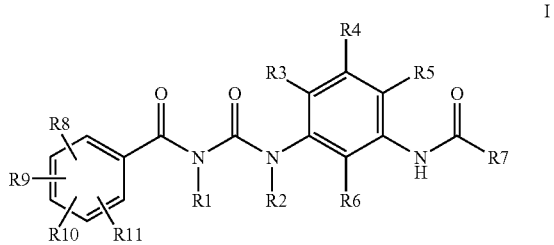

in which the radicals are defined as specified, and also to their physiologically tolerated salts. The compounds are suitable, for example, as medicaments for preventing and treating type 2 diabetes.

10 Claims, No Drawings

OTHER PUBLICATIONS

Lee Daniel W et al., Leptin agonists as a potential approach to the treatment of obestiy, Drugs of the Future, 2001, vol. 26(9), pp. 873-881.

Okada Hiroshi et al., Synthesis and Antitumor Activities of Prodrugs of Benzoylphenylureas, Chem. Pharm. Bull., 1994, vol. 42 (1), pp. 57-61.

Salvador Javier et al., Perspectives in the therapeutic use of leptin, Expert Opinion on Pharmacotherapy 2001, 2(10), 1615-1622.

T.P. Sura et al., Urea Nitrate: A Reagent For Regioselective Nitration of Aromatic Amines, Synthetic Communications, vol. 18, 1988, pp. 2161-2165.

Tyle, Praveen, Iontophoretic Devices for Drug Delivery, Pharmaceutical Research, vol. 3, No. 6, 1986 pp. 318-326.

Wang, et al., Development of a Class-Specific Competitive ELISA for the Benzoylphenylurea Insecticides, J. Agric. Food Chem. (1998) vol. 46, pp. 3330-3338.

Zunft, H. et al., Carob Pulp Preparation for Treatment of Hypercholesterolemia, Advances in Therapy, 2001, vol. 18(5), pp. 230-236.

CARBONYLAMINO-SUBSTITUTED ACYL PHENYL UREA DERIVATIVES, PROCESS FOR THEIR PREPARATION AND THEIR USE

This application claims the benefit of U.S. Provisional Application No. 60/478,757, filed Jun. 16, 2003 and priority to German Application No.DE10302452.2-42, filed Jan. 23, 2003.

DESCRIPTION

The invention relates to carbonylamino-substituted acyl phenyl urea derivatives, and also to their physiologically tolerated salts and physiologically functional derivatives.

WO 9946236 (Novo Nordisk) describes carbonylamino-substituted acyl phenyl urea derivatives (Example 1) which are effective in the event of type 2 diabetes.

WO 00/07991 (PCT/GB99/02489 Astra Zeneca) describes amide derivatives as inhibitors of the formation of cytokines.

It is an object of the invention to provide compounds which make possible prevention and treatment of type II diabetes. To this end, the compounds should in particular exhibit a therapeutically utilizable blood sugar-lowering action.

The invention therefore relates to compounds of the formula I

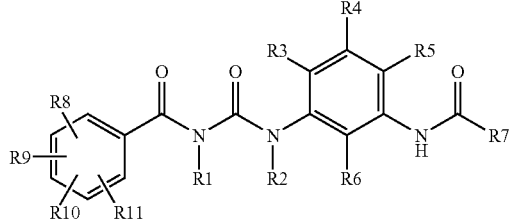

wherein

R8, R9, R10, R11 are each independently H, F, Cl, Br, OH, $NO_2$, CN, O—$(C_1-C_6)$alkyl, O—$(C_2-C_6)$alkenyl, O—$(C_2-C_6)$alkynyl, O—$SO_2$—$(C_1-C_4)$-alkyl, $(C_1-C_6)$-alkyl, $(C_2-C_6)$-alkenyl or $(C_2-C_6)$alkynyl,
  wherein said O—$(C_1-C_6)$alkyl, O—$(C_2-C_6)$alkenyl, O—$(C_2-C_6)$alkynyl, O—$SO_2$—$(C_1-C_4)$-alkyl, $(C_1-C_6)$-alkyl, $(C_2-C_6)$-alkenyl and $(C_2-C_6)$alkynyl radicals are optionally mono- or polysubstituted by F, Cl or Br;

R1, R2 are each independently H, $(C_1-C_6)$-alkyl,
  wherein said $(C_1-C_6)$-alkyl radical is optionally substituted by OH, O—$(C_1-C_4)$-alkyl, $NH_2$, $NH(C_1-C_4)$-alkyl, $N[(C_1-C_6)$-alkyl$]_2$, O—$(C_1-C_6)$-alkyl, CO—$(C_1-C_6)$-alkyl, COO—$(C_1-C_6)$-alkyl, $(C_1-C_6)$-alkylene-COOH or $(C_1-C_6)$-alkylene-COO—$(C_1-C_6)$-alkyl;

R3, R4, R5, R6 are each independently H, F, Cl, Br, $NO_2$, CN, O—R12, O-phenyl, S—R12, COOR12, N(R13)(R14), $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkylene or O—$(C_1-C_5)$-alkyl-COOR12,
  wherein said $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkylene and O—$(C_1-C_5)$-alkyl-COOR12 radicals are optionally mono- or polysubstituted by F, Cl, Br, OR12, COOR12 or N(R13)(R14);

R7 is H, $(C_1-C_6)$-alkyl, $(C_3-C_7)$-cycloalkyl, $(C_3-C_7)$-cycloalkyl-$(C_1-C_4)$-alkylene, $(C_2-C_6)$-alkenyl, $(C_2-C_6)$-alkynyl, $(C_1-C_6)$-alkylcarboxy-$(C_1-C_6)$-alkylene, COOR12, $(C_6-C_{10})$-aryl, $(C_6-C_{10})$-aryl-$(C_1-C_4)$-alkylene, heterocyclic radical, heteroaryl, heteroaryl-$(C_1-C_4)$-alkylene or heteroarylcarbonyl,
  wherein the alkyl, cycloalkyl, alkylene, alkenyl and alkynyl groups contained in said $(C_1-C_6)$-alkyl, $(C_3-C_7)$-cycloalkyl, $(C_3-C_7)$-cycloalkyl-$(C_1-C_4)$-alkylene, $(C_2-C_6)$-alkenyl, $(C_2-C_6)$-alkynyl, $(C_1-C_6)$-alkylcarboxy-$(C_1-C_6)$-alkylene, $(C_6-C_{10})$-aryl-$(C_1-C_4)$-alkylene and heteroaryl-$(C_1-C_4)$-alkylene radicals are optionally mono- or polysubstituted by F, Cl, Br, OR12, COOR12, $CONH_2$, CONH$(C_1-C_6)$-alkyl, CON[$(C_1-C_6)$-alkyl]$_2$ or N(R13)(R14), and wherein the aryl and heteroaryl groups contained in said $(C_6-C_{10})$-aryl, $(C_6-C_{10})$-aryl-$(C_1-C_4)$-alkylene, heteroaryl, heteroaryl-$(C_1-C_4)$-alkylene and heteroarylcarbonyl radicals are optionally mono- or polysubstituted by F, Cl, Br, $NO_2$, CN, O—R12, S—R12, COOR12, N(R13)(R14) or $(C_1-C_6)$-alkyl;

R12 is H, $(C_1-C_8)$-alkyl, $(C_2-C_8)$-alkenyl or $(C_2-C_8)$-alkynyl, wherein said $(C_1-C_8)$-alkyl, $(C_2-C_8)$-alkenyl and $(C_2-C_8)$-alkynyl radicals are optionally mono- or polysubstituted by F, Cl, Br, OH or O—$(C_1-C_4)$-alkyl, R13, R14 are each independently H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl,
  wherein said phenyl and $SO_2$-phenyl radicals are optionally mono- or disubstituted by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$; or R13 and R14, taken together with the nitrogen atom to which they are attached, form a 3–7 membered, saturated, heterocyclic ring which may contain up to 2 further heteroatoms from the group of N, O and S, and wherein said heterocyclic ring is optionally mono-, di- or trisubstituted by F, Cl, Br, OH, oxo, N(R21)(R22) or $(C_1-C_4)$-alkyl;

R21, R22 are each independently H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl,
  wherein said phenyl and $SO_2$-phenyl radicals are optionally mono- or disubstituted by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

with the proviso that when R5 is halogen or unsubstituted $(C_1-C_6)$-alkyl, R7 cannot be heterocyclic radical or heteroaryl;

and pharmaceutically acceptable salts thereof.

Preference is given to compounds of the formula I in which one or more radicals are defined as follows:

R8, R9, R10, R11 are each independently H, F, Cl, Br, OH, $NO_2$, CN or O—$(C_1-C_6)$-alkyl, wherein said O—$(C_1-C_6)$-alkyl radical is optionally mono- or polysubstituted by F, Cl or Br;

R1, R2 are each H;

R3, R4, R5, R6 are each independently, H, F, Cl, Br, $NO_2$, CN, O—R12, 0-phenyl, S—R12, COOR12, N(R13)

(R14), $(C_1–C_6)$-alkyl, $(C_2–C_6)$-alkenyl, $(C_2–C_6)$-alkynyl, $(C_3–C_7)$-cycloalkyl, $(C_3–C_7)$-cycloalkyl-$(C_1–C_4)$-alkylene or O—$(C_1–C_5)$-alkyl-COOR12, wherein said $(C_1–C_6)$-alkyl, $(C_2–C_6)$-alkenyl, $(C_2–C_6)$-alkynyl, $(C_3–C_7)$-cycloalkyl, $(C_3–C_7)$-cycloalkyl-$(C_1–C_4)$-alkylene and O—$(C_1–C_5)$-alkyl-COOR12 radicals are optionally mono- or polysubstituted by F, Cl, Br, OR12, COOR12 or N(R13)(R14);

R7 is H, $(C_1–C_6)$-alkyl, $(C_3–C_7)$-cycloalkyl, $(C_2–C_6)$-alkenyl, $(C_2–C_6)$-alkynyl, $(C_1–C_6)$-alkylcarboxy-$(C_1–C_6)$-alkylene, COOR12, $(C_6–C_{10})$-aryl, $(C_6–C_{10})$-aryl-$(C_1–C_4)$-alkylene, heteroaryl, heteroaryl-$(C_1–C_4)$-alkylene or heteroarylcarbonyl, wherein the alkyl, cycloalkyl, alkylene, alkenyl and alkynyl groups contained in said $(C_1–C_6)$-alkyl, $(C_3–C_7)$-cycloalkyl, $(C_2–C_6)$-alkenyl, $(C_2–C_6)$-alkynyl, $(C_1–C_6)$-alkylcarboxy-$(C_1–C_6)$-alkylene, $(C_6–C_{10})$-aryl-$(C_1–C_4)$-alkylene and heteroaryl-$(C_1–C_4)$-alkylene radicals are optionally mono- or polysubstituted by F, Cl, Br, OR12, COOR12, $CONH_2$, $CONH(C_1–C_6)$-alkyl, $CON[(C_1–C_6)$-alkyl$]_2$ or N(R13)(R14), and wherein the aryl and heteroaryl groups contained in said $(C_6–C_{10})$-aryl, $(C_6–C_{10})$-aryl-$(C_1–C_4)$-alkylene, heteroaryl, heteroaryl-$(C_1–C_4)$-alkylene and heteroarylcarbonyl radicals are optionally mono- or polysubstituted by F, Cl, Br, $NO_2$, CN, O—R12, S—R12, COOR12, N(R13)(R14) or $(C_1–C_6)$-alkyl;

R12 is H, $(C_1–C_8)$-alkyl, $(C_2–C_8)$-alkenyl or $(C_2–C_8)$-alkynyl, wherein said $(C_1–C_8)$-alkyl, $(C_2–C_8)$-alkenyl and $(C_2–C_8)$-alkynyl radicals are optionally mono- or polysubstituted by F, Cl, Br, OH or O—$(C_1–C_4)$-alkyl;

R13, R14 are each independently H, $(C_1–C_8)$-alkyl, $(C_2–C_8)$-alkenyl, $(C_2–C_8)$-alkynyl, $(C_3–C_7)$-cycloalkyl, $(C_3–C_7)$-cycloalkyl-$(C_1–C_4)$-alkylene, COO—$(C_1–C_4)$-alkyl, COO—$(C_2–C_4)$-alkenyl, phenyl or $SO_2$-phenyl, wherein said phenyl and $SO_2$-phenyl radicals are optionally mono- or disubstituted by F, Cl, CN, OH, $(C_1–C_6)$-alkyl, O—$(C_1–C_6)$-alkyl, $CF_3$, $OCF_3$, COOH, COO$(C_1–C_6)$-alkyl or $CONH_2$; or R13 and R14, taken together with the nitrogen atom to which they are attached, form a 3–7 membered, saturated, heterocyclic ring which may contain up to 2 further heteroatoms from the group of N, O and S, and wherein said heterocyclic ring is optionally mono-, di- or trisubstituted by F, Cl, Br, OH, oxo, N(R21)(R22) or $(C_1–C_4)$-alkyl;

R21, R22 are each independently H or $(C_1–C_8)$-alkyl;

with the proviso that when R5 is halogen or unsubstituted $(C_1–C_6)$-alkyl, R7 cannot be heterocyclic radical or heteroaryl;

and pharmaceutically acceptable salts thereof.

Particular preference is given to compounds of the formula I in which one or more radicals are defined as follows:

R8, R9, R10, R11 are each independently H, F or Cl;
R1, R2, R4, R6 are each H;
R3, R5 are each independently H, Cl, OR12, COOR12, N(R13)(R14) or $(C_1–C_6)$-alkyl;
R7 is $(C_1–C_6)$-alkyl, wherein said $(C_1–C_6)$-alkyl radical is optionally mono- or polysubstituted by F, OR12, COOR12 or N(R13)(R14), $(C_3–C_6)$-cycloalkyl, $(C_2–C_6)$-alkenyl, $(C_2–C_6)$-alkynyl, $(C_1–C_5)$-alkylcarboxy-$(C_1–C_6)$-alkylene, COOR12, phenyl, wherein said phenyl radical is optionally mono- or polysubstituted by F, OMe or $OCF_3$, or benzyl, wherein the phenyl ring of said benzyl radical is optionally substituted by OMe, pyridyl, thienyl, furanyl, indolylcarbonyl or benzofuranyl, wherein said benzofuranyl radical is optionally substituted by Cl or OMe;

R12 is H or $(C_1–C_8)$-alkyl, wherein said $(C_1–C_8)$-alkyl radical is optionally mono- or polysubstituted by F;

R13, R14 are each independently H or $(C_1–C_8)$-alkyl; or

R13 and R14, taken together with the nitrogen atom to which they are attached, form a 5-membered, saturated heterocyclic ring;

with the proviso that when R5 is halogen or unsubstituted $(C_1–C_6)$-alkyl, R7 cannot be heterocyclic radical or heteroaryl;

and pharmaceutically acceptable salts thereof.

The invention relates to compounds of the formula 1, in the form of their racemates, racemic mixtures and pure enantiomers, and also to their diastereomers and mixtures thereof.

The alkyl radicals in the substituents R1, R2, R3, R4, R5, R6, R7, R8, R9, R10, R11, R12, R13, R14, R21 and R22 may be either straight-chain or branched.

When radicals or substituents can occur more than once in the compounds of the formula. I, for example O—R12, they may each independently be as defined and be the same or different.

As a consequence of their higher water solubility compared to the starting or basic compounds, pharmaceutically acceptable salts are particularly suitable for medical applications. These salts have to have a pharmaceutically acceptable anion or cation. Suitable pharmaceutically acceptable acid addition salts of the compounds according to the invention are salts of inorganic acids such as hydrochloric acid, hydrobromic acid, phosphoric acid, metaphosphoric acid, nitric acid and sulfuric acid, and also of organic acids, e.g. acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts having a pharmaceutically unacceptable anion, for example trifluoroacetate, are likewise encompassed by the scope of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I according to the invention, e.g. an ester which is able, on administration to a mammal, e.g. a human, to (directly or indirectly) form a compound of the formula I or an active metabolite thereof.

The physiologically functional derivatives also include prodrugs of the compounds according to the invention, for example as described in H. Okada et al., Chem. Pharm. Bull. 1994, 42, 57–61. Such prodrugs can be metabolized in vivo to a compound according to the invention. These prodrugs may or may not be active themselves.

The compounds according to the invention can also exist in different polymorphous forms, for example as amorphous and crystalline polymorphous forms. All polymorphous forms of the compounds according to the invention are encompassed by the scope of the invention and are a further aspect of the invention.

All references given below to "compound(s) of formula I" refer to compound(s) of the formula I as described above, and also to their salts, solvates and physiologically functional derivatives as described herein.

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

In this context, an aryl radical is a phenyl, naphthyl, biphenyl, tetrahydronaphthyl, alpha- or beta-tetralon, indanyl or indan-1-onyl radical.

The terms "heterocyclic ring" and "heterocyclic radical" used herein relate to heteroaryl radicals and heterocycloalkyl radicals which derive from 3 to 10 membered carbon rings in which one or more carbon atoms are replaced by one or more atoms selected from the group of oxygen, sulfur and nitrogen.

Suitable "heterocyclic rings" and "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, fu ryl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is either 2-, 3- or 4-pyridyl. Thienyl is either 2- or 3-thienyl. Furyl is either 2- or 3-furyl.

Also included are the corresponding N-oxides of these compounds, for example 1-oxy-2-, 3- or 4-pyridyl.

Also included are one or more benzofused derivatives of these heterocycles.

The compound(s) of the formula (I) can also be administered in combination with further active ingredient.

The amount of a compound of formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg and 50 mg) per day per kilogram of bodyweight, for example 3–10 mg/kg/day. An intravenous dose may, for example, be in the range from 0.3 mg to 1.0 mg/kg and may advantageously be administered as an infusion of from 10 ng to 100 ng per kilogram per minute. Suitable infusion solutions for these purposes may, for example, contain from 0.1 ng to 10 mg, typically from 1 ng to 10 mg, per milliliter. Individual doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of formula 1. The pharmaceutical compositions according to the invention may be produced by one of the known pharmaceutical methods which consist essentially of mixing the ingredients with pharmacologically acceptable carriers and/or excipients.

Pharmaceutical compositions according to the invention are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a certain amount of the compound of formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are prepared by uniform and homogeneous mixing of the active ingredient with a liquid and/or finely divided solid carrier, after which the product is shaped if necessary. For example, a tablet can be produced by compressing or shaping a powder or granules of the compound, optionally with one or more additional ingredients. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain the compound of formula I with a flavoring, customarily sucrose, and gum arabic or tragacanth, and pastilles which include the compound in an inert base such as gelatin and glycerol or sucrose and gum arabic.

Suitable pharmaceutical compositions for parenteral administration include preferably sterile aqueous preparations of a compound of formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. The injectable compositions according to the invention generally contain from 0.1 to 5% by weight of the active compound.

Suitable pharmaceutical compositions for rectal administration are preferably in the form of single dose suppositories. These can be prepared by mixing a compound of formula I with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters advantageously contain the active ingredient in an optionally buffered aqueous solution, dissolved and/or dispersed in a tackifier or dispersed in a polymer. A suitable active ingredient concentration is from approx. 1% to 35%, preferably from approx. 3 to 15%. A particular means of releasing the active ingredient is by electrotransport or iontophoresis, as described, for example, in Pharmaceutical Research, 2(6): 318 (1986).

Further useful active ingredients for combination products are as follows: All antidiabetics mentioned in the Rote Liste 2001, chapter 12. They can be combined with the compounds of the formula I according to the invention, in particular for synergistic enhancement of the action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Antidiabetics include insulin and insulin derivatives, for example Lantus® (see www.lantus.com) or HMR 1964, fast-acting insulins (see U.S. Pat. No. 6,221,633), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In another embodiment of the invention, the compounds of the formula I are administered in combination with a cholesterol absorption inhibitor, for example, ezetimibe, tiqueside, pamaqueside.

In another embodiment of the invention, the compounds of the formula I are administered in combination with a PPAR gamma agonist, for example, rosiglitazone, pioglitazone, JTT-501, GI 262570.

In another embodiment of the invention, the compounds of the formula I are administered in combination with PPAR alpha agonist, for example, GW 9578, GW 7647.

In another embodiment of the invention, the compounds of the formula I are administered in combination with a mixed PPAR alpha/gamma agonist, for example, GW 1536, AVE 8042, AVE 8134, AVE 0847, or as described in PCT/US 11833, PCT/US 11490, DE10142734.4.

In another embodiment of the invention, the compounds of the formula I are administered in combination with a fibrate, for example, fenofibrate, clofibrate, bezafibrate.

In another embodiment of the invention, the compounds of the formula I are administered in combination with an MTP inhibitor, for example, implitapide, BMS-201038, R-103757.

In another embodiment of the invention, the compounds of the formula I are administered in combination with bile acid absorption inhibitor (see, for example, U.S. Pat. No. 6,245,744 or U.S. Pat. No. 6,221,897), for example, HMR 1741.

In another embodiment of the invention, the compounds of the formula I are administered in combination with a CETP inhibitor, for example, JTT-705.

In another embodiment of the invention, the compounds of the formula I are administered in combination with a polymeric bile acid adsorbent, for example, cholestyramine, colesevelam.

In another embodiment of the invention, the compounds of the formula I are administered in combination with an LDL receptor inducer (see U.S. Pat. No. 6,342,512), for example, HMR1171, HMR1586.

In another embodiment of the invention, the compounds of the formula I are administered in combination with an ACAT inhibitor, for example, avasimibe.

In another embodiment of the invention, the compounds of the formula I are administered in combination with an antioxidant, for example, OPC-14117.

In another embodiment of the invention, the compounds of the formula I are administered in combination with a lipoprotein lipase inhibitor, for example, NO-1886.

In another embodiment of the invention, the compounds of the formula I are administered in combination with an ATP-citrate lyase inhibitor, for example, SB-204990.

In another embodiment of the invention, the compounds of the formula I are administered in combination with a squalene synthetase inhibitor, for example, BMS-188494.

In another embodiment of the invention, the compounds of the formula I are administered in combination with a lipoprotein(a) antagonist, for example, Cl-1027 or nicotinic acid.

In another embodiment of the invention, the compounds of the formula I are administered in combination with a lipase inhibitor, for example, orlistat.

In another embodiment of the invention, the compounds of the formula I are administered in combination with insulin.

In another embodiment, the compounds of the formula I are administered in combination with a sulfonylurea, for example, tolbutamide, glibenclamide, glipizide or glimepiride.

In another embodiment, the compounds of the formula I are administered in combination with a biguanide, for example, metformin.

In yet another embodiment, the compounds of the formula I are administered in combination with a meglitinide, for example, repaglinide.

In another embodiment, the compounds of the formula I are administered in combination with a thiazolidinedione, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, for example, miglitol or acarbose.

In another embodiment, the compounds of the formula I are administered in combination with an active ingredient which acts on the ATP-dependent potassium channel of the beta cells, for example, tolbutamide, glibenclamide, glipizide, glimepiride or repaglinide.

In another embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554–558), NPY antagonists, e.g. naphthalene-1-sulfonic acid {4-[(4-aminoquinazolin-2-ylamino)methyl]cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5] naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, P3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In another embodiment of the invention, the other active ingredient is leptin, see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In another embodiment, the other active ingredient is dexamphatamine or amphetamine.

In another embodiment, the other active ingredient is fenfluramine or dexfenfluramine.

In another embodiment, the other active ingredient is sibutramine.

In another embodiment, the other active ingredient is orlistat.

In another embodiment, the other active ingredient is mazindol or phentermine.

In another embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230–6.) Caromax® is a carob-containing product supplied by Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromaxe can also be administered in the form of foodstuffs, for example, in bakery products or muesli bars.

It will be appreciated that any suitable combination of the compounds according to the invention with one or more of the above-mentioned compounds and optionally one or more further pharmacologically active substances is regarded as being covered by the scope of protection of the present invention.

The citation of any reference herein should not be construed as an admission that such reference is available as "Prior Art" to the instant application.

Various publications are cited herein, the disclosures of which are incorporated by reference in their entireties.

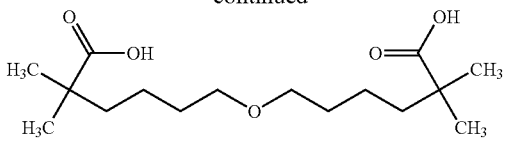

Cl-1027

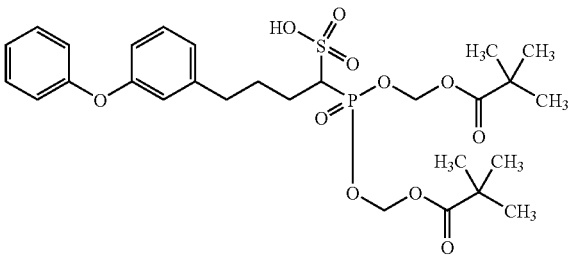

BMS-188494

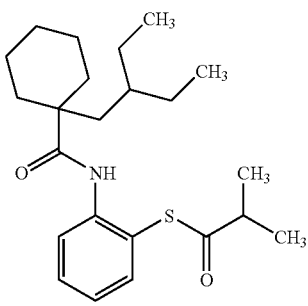

JTT-705

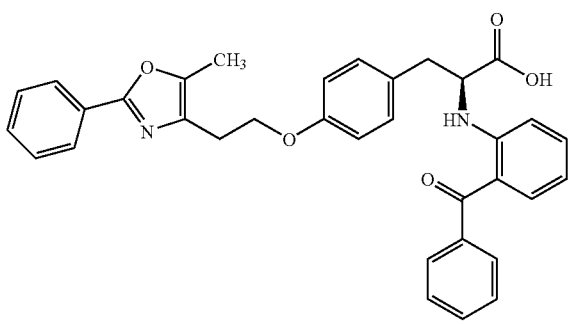

GI 262570

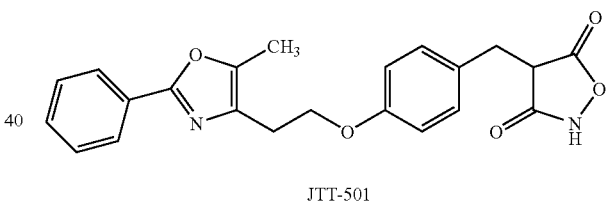

JTT-501

The examples recited hereinbelow serve to illustrate the invention, but without restricting it.

No example which is exactly analogous to compounds of the formula I is cited in WO 9946236. Example A was therefore selected as the most similar compound. The compounds of this application are distinguished from Comparative Example A are distinguished by an increased activity on glycogen phosphorylase a, see Table 2.

COMPARATIVE EXAMPLE A

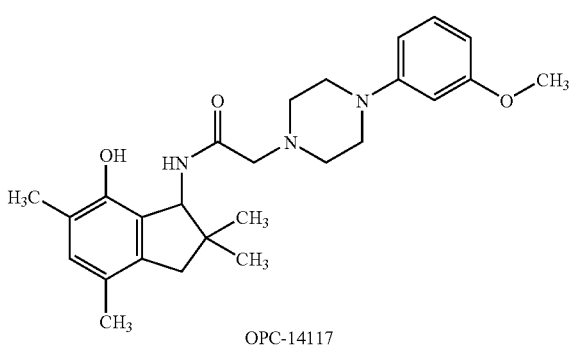

OPC-14117

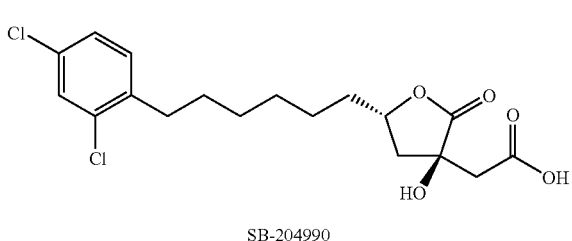

SB-204990

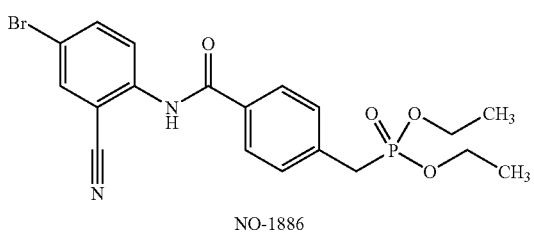

NO-1886

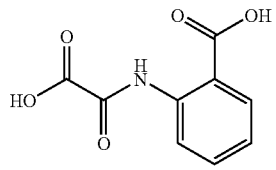

TABLE 1

Examples of the formula I

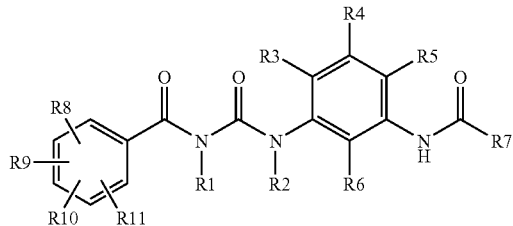

I

| Ex. | R1 | R2 | R3 | R4 | R5 | R6 | R7 | R8, R9, R10, R11 |
|---|---|---|---|---|---|---|---|---|
| 1 | H | H | $OCH_3$ | H | H | H | $CH_3$ | 2-Cl, 4-F, 5-F, H |
| 2 | H | H | $OCH_3$ | H | H | H | $COOCH_3$ | 2-Cl, 4-F, 5-F, H |
| 3 | H | H | $OCH_3$ | H | H | H | $CH_2COOCH_3$ | 2-Cl, 4-F, 5-F, H |
| 4 | H | H | $OCH_3$ | H | H | H | $CH_2CH_2COOCH_3$ | 2-Cl, 4-F, 5-F, H |
| 5 | H | H | $OCH_3$ | H | H | H | COOH | 2-Cl, 4-F, 5-F, H |
| 6 | H | H | $OCH_3$ | H | H | H | $CH_2COOH$ | 2-Cl, 4-F, 5-F, H |
| 7 | H | H | $OCH_3$ | H | H | H | $CH_2CH_2COOH$ | 2-Cl, 4-F, 5-F, H |
| 8 | H | H | $OCH_3$ | H | H | H | $CH_2CH_2CONH_2$ | 2-Cl, 4-F, 5-F, H |
| 9 | H | H | $CH_3$ | H | $OCH_3$ | H | $CH_3$ | 2-Cl, 4-F, 5-F, H |
| 10 | H | H | $CH_3$ | H | $OCH_3$ | H | $CH_2COOCH_3$ | 2-Cl, 4-F, 5-F, H |
| 11 | H | H | $CH_3$ | H | $OCH_3$ | H | $CH_2COOH$ | 2-Cl, 4-F, 5-F, H |
| 12 | H | H | $CH_3$ | H | $OCH_3$ | H | $CH_2CH_2COOH$ | 2-Cl, 4-F, 5-F, H |
| 13 | H | H | $CH_3$ | H | $OCH_3$ | H | COOH | 2-Cl, 4-F, 5-F, H |
| 14 | H | H | $OCH_3$ | H | $CH_3$ | H | $CH_3$ | 2-Cl, 4-F, 5-F, H |
| 15 | H | H | $OCH_3$ | H | $CH_3$ | H | $COOCH_3$ | 2-Cl, 4-F, 5-F, H |
| 16 | H | H | $OCH_3$ | H | $CH_3$ | H | $CH_2COOCH_3$ | 2-Cl, 4-F, 5-F, H |
| 17 | H | H | $OCH_3$ | H | $CH_3$ | H | COOH | 2-Cl, 4-F, 5-F, H |
| 18 | H | H | $OCH_3$ | H | $CH_3$ | H | $CH_2COOH$ | 2-Cl, 4-F, 5-F, H |
| 19 | H | H | $OCH_3$ | H | COOH | H | $CH_3$ | 2-Cl, 4-F, 5-F, H |
| 20 | H | H | $OCH_3$ | H | $COOCH_2CH_3$ | H | $CH_3$ | 2-Cl, 4-F, 5-F, H |
| 21 | H | H | $OCH_3$ | H | $COOCH_2CH_3$ | H | $CH_2COOCH_3$ | 2-Cl, 4-F, 5-F, H |
| 22 | H | H | $OCH_3$ | H | COOH | H | $CH_2COOH$ | 2-Cl, 4-F, 5-F, H |
| 23 | H | H | $OCH_3$ | H | $COOCH_2CH_3$ | H | $COOCH_3$ | 2-Cl, 4-F, 5-F, H |
| 24 | H | H | $OCH_3$ | H | $COOCH_2CH_3$ | H | $CH_2CH_2COOCH_3$ | 2-Cl, 4-F, 5-F, H |
| 25 | H | H | $OCH_3$ | H | COOH | H | COOH | 2-Cl, 4-F, 5-F, H |
| 26 | H | H | $OCH_3$ | H | COOH | H | $CH_2CH_2COOH$ | 2-Cl, 4-F, 5-F, H |
| 27 | H | H | $OCH_3$ | H | H | H | $CH_2OCH_3$ | 2-Cl, 4-F, 5-F, H |
| 28 | H | H | $OCH_3$ | H | H | H | 3-Pyrindinyl | 2-Cl, 4-F, 5-F, H |
| 29 | H | H | $OCH_3$ | H | H | H | 2-Thienyl | 2-Cl, 4-F, 5-F, H |
| 30 | H | H | $OCH_3$ | H | H | H | $CH_2CH_3$ | 2-Cl, 4-F, 5-F, H |
| 31 | H | H | $OCH_3$ | H | H | H | Cyclopropyl | 2-Cl, 4-F, 5-F, H |
| 32 | H | H | $OCH_3$ | H | H | H | 2-Furanyl | 2-Cl, 4-F, 5-F, H |
| 33 | H | H | $OCH_3$ | H | H | H | Cyclopentyl | 2-Cl, 4-F, 5-F, H |
| 34 | H | H | $OCH_3$ | H | H | H | 2-Methoxyphenyl | 2-Cl, 4-F, 5-F, H |
| 35 | H | H | $OCH_3$ | H | H | H | 1-Propen-1-yl | 2-Cl, 4-F, 5-F, H |
| 36 | H | H | $OCH_3$ | H | H | H | 2-Fluorophenyl | 2-Cl, 4-F, 5-F, H |
| 37 | H | H | $OCH_3$ | H | H | H | Benzyl | 2-Cl, 4-F, 5-F, H |
| 38 | H | H | $OCH_3$ | H | H | H | 5-Methoxy-benzofuran-2-yl | 2-Cl, 4-F, 5-F, H |
| 39 | H | H | $OCH_3$ | H | H | H | 5-Chlorobenzofuran-2-yl | 2-Cl, 4-F, 5-F, H |
| 40 | H | H | $OCH_3$ | H | H | H | 4-Fluorophenyl | 2-Cl, 4-F, 5-F, H |
| 41 | H | H | $OCH_3$ | H | H | H | 3-Methoxyphenylmethyl | 2-Cl, 4-F, 5-F, H |
| 42 | H | H | $OCH_3$ | H | H | H | 1H-indol-3-yl-carbonyl | 2-Cl, 4-F, 5-F, H |
| 43 | H | H | $OCH_3$ | H | H | H | Isopropyl | 2-Cl, 4-F, 5-F, H |
| 44 | H | H | $OCH_3$ | H | H | H | Cyclobutyl | 2-Cl, 4-F, 5-F, H |
| 45 | H | H | $OCH_3$ | H | H | H | 3-Fluorophenyl | 2-Cl, 4-F, 5-F, H |
| 46 | H | H | $OCH_3$ | H | H | H | I-Buten-4-yl | 2-Cl, 4-F, 5-F, H |
| 47 | H | H | $OCH_3$ | H | H | H | n-Bu | 2-Cl, 4-F, 5-F, H |
| 48 | H | H | $OCH_3$ | H | H | H | $(CH_2)_2COOCH_2CH_3$ | 2-Cl, 4-F, 5-F, H |
| 49 | H | H | $OCH_3$ | H | H | H | $CH_2OCOCH_3$ | 2-Cl, 4-F, 5-F, H |
| 50 | H | H | $OCH_3$ | H | H | H | i-Pr | 2-Cl, 4-F, 5-F, H |
| 51 | H | H | $OCH_3$ | H | H | H | 2-Trifluoromethoxyphenyl | 2-Cl, 4-F, 5-F, H |
| 52 | H | H | $OCH_3$ | H | H | H | $CH_2NH_2$ | 2-Cl, 4-F, 5-F, H |
| 53 | H | H | $OCH_3$ | H | H | H | $(CH_2)_3NH_2$ | 2-Cl, 4-F, 5-F, H |
| 54 | H | H | $OCH_3$ | H | H | H | Methylaminomethyl | 2-Cl, 4-F, 5-F, H |
| 55 | H | H | $OCH_3$ | H | H | H | $(CH_2)_2NH_2$ | 2-Cl, 4-F, 5-F, H |

TABLE 1-continued

Examples of the formula I

I

[Structure of formula I with substituents R1-R11 on a central aromatic ring with amide/urea linkages]

| Ex. | R1 | R2 | R3 | R4 | R5 | R6 | R7 | R8, R9, R10, R11 |
|---|---|---|---|---|---|---|---|---|
| 56 | H | H | OCH$_3$ | H | H | H | [structure: CH with NH$_2$ and HO groups] | 2-Cl, 4-F, 5-F, H |
| 57 | H | H | OCH$_3$ | H | H | H | 1-Butyn-4-yl | 2-Cl, 4-F, 5-F, H |
| 58 | H | H | OCH$_3$ | H | H | H | CH$_2$N(CH$_3$)$_2$ | 2-Cl, 4-F, 5-F, H |
| 59 | H | H | OCH$_3$ | H | H | H | Ethoxymethyl | 2-Cl, 4-F, 5-F, H |
| 60 | H | H | OCH$_3$ | H | H | H | Propargyl | 2-Cl, 4-F, 5-F, H |
| 61 | H | H | OCH$_3$ | H | H | H | CHF$_2$ | 2-Cl, 4-F, 5-F, H |
| 62 | H | H | OCH$_3$ | H | H | H | CH$_2$OH | 2-Cl, 4-F, 5-F, H |
| 63 | H | H | OCH$_3$ | H | COOCH$_3$ | H | CH$_2$COOCH$_3$ | 2-Cl, 4-F, 5-F, H |
| 64 | H | H | OCF$_3$ | H | H | H | CH$_3$ | 2-Cl, 4-F, 5-F, H |
| 65 | H | H | OCF$_3$ | H | H | H | COOCH$_3$ | 2-Cl, 4-F, 5-F, H |
| 66 | H | H | OCF$_3$ | H | H | H | CH$_2$COOCH$_3$ | 2-Cl, 4-F, 5-F, H |
| 67 | H | H | OCF$_3$ | H | H | H | CH$_2$CH$_2$COOCH$_3$ | 2-Cl, 4-F, 5-F, H |
| 68 | H | H | OCF$_3$ | H | H | H | COOH | 2-Cl, 4-F, 5-F, H |
| 69 | H | H | OCF$_3$ | H | H | H | CH$_2$COOH | 2-Cl, 4-F, 5-F, H |
| 70 | H | H | OCF$_3$ | H | H | H | CH$_2$CH$_2$COOH | 2-Cl, 4-F, 5-F, H |
| 71 | H | H | N(CH$_3$)$_2$ | H | H | H | CH$_3$ | 2-Cl, 4-F, 5-F, H |
| 72 | H | H | N(CH$_2$CH$_3$)$_2$ | H | H | H | CH$_3$ | 2-Cl, 4-F, 5-F, H |
| 73 | H | H | N-Pyrrolidinyl | H | H | H | CH$_3$ | 2-Cl, 4-F, 5-F, H |
| 74 | H | H | N(CH$_3$)$_2$ | H | H | H | CH$_2$COOCH$_3$ | 2-Cl, 4-F, 5-F, H |
| 75 | H | H | N-Pyrrolidinyl | H | H | H | CH$_2$COOCH$_3$ | 2-Cl, 4-F, 5-F, H |
| 76 | H | H | N(CH$_3$)$_2$ | H | H | H | CH$_2$COOH | 2-Cl, 4-F, 5-F, H |
| 77 | H | H | N-Pyrrolidinyl | H | H | H | CH$_2$COOH | 2-Cl, 4-F, 5-F, H |
| 78 | H | H | H | H | H | H | CH$_2$CH$_2$COOH | 2-Cl, 4-Cl, H, H |
| 79 | H | H | H | H | H | H | (CH$_2$)$_3$NH$_2$ | 2-Cl, 4-Cl, H, H |
| 80* | H | H | Cl | H | H | H | CH$_3$ | 2-Cl, 4-Cl, H, H |
| 81 | H | H | Cl | H | H | H | CH$_2$CH$_2$COOH | 2-Cl, 4-Cl, H, H |
| 82 | H | H | OCH$_3$ | H | H | H | CH$_3$ | 2-Cl, 4-Cl, H, H |
| 83 | H | H | OCH$_3$ | H | H | H | CH$_2$CH$_2$COOH | 2-Cl, 4-Cl, H, H |
| 84 | H | H | Cl | H | H | H | CH$_2$CH$_2$COOH | 2-Cl, 4-F, 5-F, H |
| 85 | H | H | Cl | H | H | H | CH$_3$ | 2-Cl, 4-F, 5-F, H |
| 86 | H | H | Cl | H | H | H | CH$_2$COOH | 2-Cl, 4-F, 5-F, H |
| 87 | H | H | Cl | H | H | H | COOCH$_3$ | 2-Cl, 4-F, 5-F, H |
| 88 | H | H | Cl | H | H | H | COOH | 2-Cl, 4-F, 5-F, H |

*Present as the trifluoroacetic acid salt

For all the example cited, a mass spectrum or HPLC/MS was measured and the molecular peak (molecular mass+H$^+$) was detected.

The effectiveness of the compounds was tested as follows:

Glycogen Phophorylase a Activity Test

The effect of compounds on the activity of the active form of glycogen phosphorylase (GPa) was measured in the reverse direction by monitoring the synthesis of glycogen from glucose 1-phosphate by determining the release of inorganic phosphate. All reactions were carried out as duplicate determinations in 96-well microtiter plates (half area plates, Costar No. 3696), and the change in absorption as a consequence of the formation of the reaction product was measured at the wavelength specified below in a Multiskan Ascent Elisa Reader (Lab Systems, Finland).

In order to measure the GPa enzyme activity in the reverse direction, the conversion of glucose 1-phosphate to glycogen and inorganic phosphate was measured by the general method of Engers et al. (Engers HD, Shechosky S, Madsen NB, Can J Biochem 1970 July;48(7):746–754) with the following modifications: human glycogen phosphorylase a (for example containing 0.76 mg of protein/ml (Aventis Pharma Deutschland GmbH), dissolved in buffer solution E (25 mM P-glycerophosphate, pH 7.0, 1 mM EDTA and 1 mM dithiotreitol) was diluted to a concentration of 10 μg of protein/ml with buffer T (50 mM Hepes, pH 7.0, 100 mM KCl, 2.5 mM EDTA, 2.5 mM MgCl$_2$.6H$_2$O) and addition of 5 mg/ml of glycogen. Test substances were prepared as a 10 mM solution in DMSO and diluted to 50 μM with buffer solution T. To 10 μl of this solution were added 10 μl of 37.5 mM glucose dissolved in buffer solution T and 5 mg/ml of glycogen, and also 10 μl of a solution of human glycogen phosphorylase a (10 μg of protein/ml) and 20 μl of 2.5 mM glucose 1-phosphate. The base value of the activity of glycogen phosphorylase a in the absence of test substance was determined by adding 10 μl of buffer solution T (0.1% DMSO). The mixture was incubated at room temperature for 40 minutes and the released inorganic phosphate was determined by means of the general method of Drueckes et al. (Drueckes P, Schinzel R, Palm D, Anal Biochem 1995 Sep. 1;230(1):173–177) with the following modifications: 50 μl of a stop solution of 7.3 mM of ammonium molybdate, 10.9 mM of zinc acetate, 3.6% of ascorbic acid, 0.9% of SDS are added to 50 μl of the enzyme mixture. After 60 minutes of incubation at 45° C., the absorption was measured at 820 nm. To determine the background absorption, the stop solution was added immediately after the addition of the glucose 1-phosphate solution in a separate reaction. This test was carried out at a concentration of 10 μM of the test substance, in order to determine the respective inhibition of glycogen phosphorylase a by the test substance in vitro.

TABLE 2

Biological activity

| Ex. | % Inhibition at 10 μM |
|---|---|
| 1 | 99 |
| 2 | 99 |
| 3 | 104 |
| 4 | 97 |
| 5 | 99 |
| 6 | 100 |
| 7 | 100 |
| 8 | 100 |
| 10 | 95 |
| 11 | 96 |
| 12 | 90 |
| 13 | 94 |
| 14 | 91 |
| 15 | 101 |
| 16 | 95 |
| 17 | 100 |
| 18 | 99 |
| 19 | 97 |
| 20 | 95 |
| 22 | 96 |
| 25 | 95 |
| 26 | 97 |
| 27 | 98 |
| 28 | 89 |
| 29 | 98 |
| 30 | 101 |
| 31 | 98 |
| 32 | 102 |
| 33 | 96 |
| 34 | 97 |
| 35 | 99 |
| 36 | 101 |
| 37 | 101 |
| 38 | 102 |
| 39 | 101 |
| 40 | 98 |
| 41 | 104 |
| 42 | 83 |
| 43 | 98 |
| 44 | 101 |
| 45 | 97 |
| 46 | 102 |
| 47 | 105 |
| 48 | 97 |
| 49 | 99 |
| 50 | 94 |
| 51 | 92 |
| 52 | 101 |
| 53 | 100 |
| 54 | 100 |
| 55 | 100 |
| 56 | 99 |
| 57 | 99 |
| 58 | 99 |
| 59 | 103 |
| 60 | 103 |
| 61 | 100 |
| 62 | 101 |
| 64 | 101 |
| 65 | 98 |
| 66 | 100 |
| 67 | 101 |
| 68 | 101 |
| 69 | 100 |
| 70 | 99 |
| 71 | 97 |
| 72 | 96 |
| 73 | 97 |
| 74 | 98 |
| 75 | 100 |
| 76 | 99 |
| 77 | 98 |
| 78 | 86 |
| 79 | 80 |
| 80 | 98 |
| 81 | 97 |
| 82 | 102 |
| 83 | 103 |
| 84 | 100 |
| 85 | 98 |
| 86 | 95 |
| 87 | 96 |
| 88 | 97 |

Comparative Example A exhibits no inhibition at a concentration of 10 μM and 11% inhibition at a concentration of 100 μM.

It can be seen from the Table that the compounds of the formula I inhibit the activity of glycogenphosphorylase a and are therefore very suitable for lowering the blood sugar level. In particular, the compounds of the formula I exhibit distinctly increased action compared to Comparative Example A.

The preparation of some examples is described in detail hereinbelow, and the remaining compounds of the formula I were obtained in a similar manner:

EXPERIMENTAL SECTION

Example 1

N-{3-[3-(2-Chloro-4,5-difluorobenzoyl)ureido]-4-methoxyphenyl}acetamide a) 2-Chloro-4,5-difluorobenzoyl isocyanate 2-Chloro-4,5-difluorobenzamide was dissolved in dichloromethane, admixed with 1.5 eq. of oxalyl chloride and heated to reflux for 16 hours. The reaction mixture was concentrated under high vacuum and reacted in stage b without further purification.

b) 1-(2-Chloro-4,5-difluorobenzoyl)-3-(2-methoxy-5-nitrophenyl)urea 1 g (5.9 mmol) of 2-methoxy-5-nitroaniline were admixed with 1.3 g (5.9 mmol) of 2-chloro-4,5-difluorobenzoyl isocyanate from stage a in 2 ml of N-methylpyrrolidone and reacted at room temperature for one hour. The precipitate was filtered off, washed twice with 5 ml of acetonitrile each time and dried under high vacuum. 2.2 g of the desired product were obtained which were used in stage c without further purification.

c) 1-(2-Chloro-4,5-difluorobenzoyl)-3-(5-amino-2-methoxyphenyl)urea 2.2 g (5.7 mmol) of 1-(2-chloro-4,5-difluorobenzoyl)-3-(2-methoxy-5-nitrophenyl)urea were heated to the boiling temperature in 50 ml of ethyl acetate and admixed with 6.4 g (28.5 mmol) of $SnCl_2$ monohydrate. After 1 hour, the mixture was allowed to cool to room temperature and the pH was adjusted to 8 using 2 N sodium hydroxide solution. The precipitate which formed was filtered off and washed with methanol, and the mother liquor was washed twice with $H_2O$, dried and concentrated under reduced pressure. The resulting product (1.4 g) was reacted in step d without further purification.

d) N-{3-[3-(2-Chloro-4,5-difluorobenzoyl)ureido]-4-methoxyphenyl}acetamide 0.10 g (0.3 mmol) of 1-(2-chloro-4,5-difluorobenzoyl)-3-(5-amino-2-methoxyphenyl)urea was admixed with 1 ml of N-methylpyrrolidone, 0.11 g (0.3 mmol) of acetic anhydride and stirred at room temperature for 2 hours. The mixture was diluted with 20 ml of $H_2O$ and extracted three times with 20 ml of ethyl acetate each time. The combined organic phase was washed with $H_2O$, concentrated and dried. The crude product was purified by preparative HPLC (column: Waters Xterra™ MS $C_{18}$, 5 µm, 30×100 mm, eluent: A: $H_2O$+0.2% trifluoroacetic acid, B: acetonitrile, gradient: 2.5 minutes 90% A/10% B to 17.5 minutes 10% A/90% B). 0.03 g of the desired product was obtained.

Melting point 225–228° C.

In a similar manner to Example 1, Examples 2–8, 27–62 and 78–88 were prepared from the corresponding nitroanilines and the corresponding isocyanates, if necessary with the use of appropriate protecting group techniques.

Example 64

N-{3-[3-(2-Chloro-4,5-difluorobenzoyl)ureido]-4-trifluoromethoxyphenyl}acetamide a) 3-Nitro-4-trifluoromethoxyaniline Method according to *Syn. Commun.* 1988, 18 (16+17), 2161–2165 3.0 g (17 mmol) of 4-trifluoromethoxyaniline were dissolved in 10 ml of conc. sulfuric acid, cooled to 0–10° C. and admixed in portions with 2.1 g (17 mmol) of urea nitrate, in such a way that the temperature did not exceed 10° C. After the addition had ended, stirring was continued for 10 minutes and then the solution was poured into ice. The mixture was extracted using dichloromethane, the combined organic phases were dried and the solvent was distilled off under reduced pressure. The product was used in the next stage without further purification (yield 2.8 g, 75%).

The 3-nitro-4-trifluoromethoxyaniline obtained in this way was reacted with acetyl chloride in a similar manner to method d for Example 1, hydrogenated with hydrogen in the presence of Pd/C and reacted with 2-chloro-4,5-difluorobenzoyl isocyanate to give the acyl urea.

Melting point 216–218° C.

In a similar manner, Examples 65 to 70 were prepared by using other acylating agents in accordance with Example 1d.

Example 73

N-{3-[3-(2-Chloro-4,5-difluorobenzoyl)ureido]-4-pyrrolidin-1-ylphenyl}acetamide a) N-(2-Fluoro-5-nitrophenyl)acetamide 5.0 g (32 mmol) of 2-fluoro-5-nitroaniline were admixed with 10 ml (110 mmol) of acetic anhydride and 0.1 ml of conc. sulfuric acid and stirred at 100° C. for 1.5 hours. The solution was added to 100 ml of ice/water, and the precipitate which formed was filtered off and washed with water. The crude product was purified by chromatography (1:1 ethyl acetate/heptane) on silica gel (yield 5.4 g, 85%).

Melting point 174–176° C.

b) N-(5-Nitro-2-pyrrolidin-1-ylphenyl)acetamide 0.5 g (2.5 mmol) of N-(2-fluoro-5-nitrophenyl)acetamide was admixed in a pressure reaction vessel with 1 ml (12.6 mmol) of pyrrolidine and stirred at 90° C. for 2.5 hours. After the mixture had been cooled, it was diluted with 20 ml of dichloromethane, adjusted to pH 4 using citric acid solution (10%) and washed four times with water. After the organic phase had been dried, the solvent was removed under reduced pressure. In the aqueous phase, a solid is precipitated out. It was filtered off with suction and washed with water, and combined with the residue from the organic phase (yield 0.58 g, 93%). The product was reacted in stage c without further purification.

Melting point 210–213° C.

c) 5-Nitro-2-pyrrolidin-1-ylaniline 0.58 g (2.3 mmol) of N-(5-nitro-2-pyrrolidin-1-ylphenyl)acetamide was admixed with 12 ml of conc. hydrochloric acid and heated to reflux for 1.5 hours. The solution was added to 100 ml of ice/water, neutralized with 2 N sodium hydroxide solution and admixed three times with ethyl acetate. After the mixture had been dried, the solvent was distilled off under reduced pressure to obtain the product quantitatively as a red solid which was used for the reactions a-d described in Example 1 without further purification (reaction with the acyl isocyanate, reduction with $SnCl_2$ and acylation with $Ac_2O$).

Melting point 175–180° C.

In a similar manner to Example 73, Examples 71, 72 and 74–77 were prepared from the corresponding amines and the particular acylating agents, if necessary with the use of customary protecting group techniques.

In the synthesis of Examples 19–26 and 63, 4-amino-3-methoxybenzoic acid was nitrated with urea nitrate in a similar manner to Example 64a. The synthetic route which followed proceeded in a similar manner to that described in Example 1.

To synthesize Examples 9–18, N-(4-methoxy-2-methylphenyl)acetamide or N-(2-methoxy-4-methylphenyl)acetamide were nitrated under customary conditions ($HNO_3$/HOAc), the amide was hydrolyzed using conc. hydrochloric acid (in a similar manner to Example 73c) and reacted further as described for Example 1.

We claim:

1. A compounds of formula I

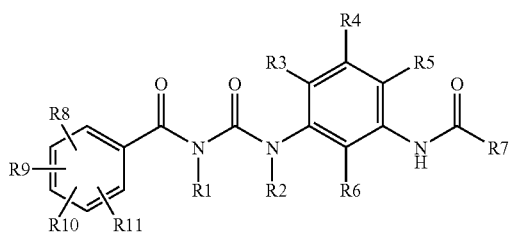

wherein
R8, R9, R10, R11 are each independently H, F, Cl, Br, OH, $NO_2$, CN, O-($C_1$–$C_6$)alkyl, O—($C_2$–$C_6$)alkenyl, O—($C_2$–$C_6$)alkynyl, O—$SO_2$—($C_1$–$C_4$)-alkyl, ($C_1$–$C_6$)-alkyl, ($C_2$–$C_6$)-alkenyl or ($C_2$–$C_6$)alkynyl,
wherein said O—($C_1$–$C_6$)alkyl, O—($C_2$–$C_6$)alkenyl, O—($C_2$–$C_6$)alkynyl, O—$SO_2$—($C_1$–$C_4$)-alkyl, ($C_1$–$C_6$)-alkyl, ($C_2$–$C_6$)-alkenyl and ($C_2$–$C_6$)alkynyl radicals are optionally mono- or polysubstituted by F, Cl or Br;

R1, R2 are each independently H, ($C_1$–$C_6$)-alkyl,
wherein said ($C_1$–$C_6$)-alkyl radical is optionally substituted by OH, O—($C_1$–$C_4$)-alkyl, $NH_2$, NH($C_1$–$C_4$)-alkyl, N[($C_1$–$C_6$)-alkyl]$_2$, O—($C_1$–$C_6$)-alkyl, CO—($C_1$–$C_6$)-alkyl, COO—($C_1$–$C_6$)-alkyl, ($C_1$–$C_6$)-alkyl, ($C_1$–$C_6$)-alkylene-COOH or ($C_1$–$C_6$)-alkylene-COO—($C_1$–$C_6$)-alkyl;

R3, R4, R5, R6 are each independently H, F, Cl, Br, $NO_2$, CN, O—R12, O-phenyl, S—R12, COOR12, N(R13)(R14), ($C_1$–$C_6$)-alkyl, ($C_2$–$C_6$)-alkenyl, ($C_2$–$C_6$)-alkynyl, ($C_3$–$C_7$)-cycloalkyl, ($C_3$–$C_7$)-cycloalkyl-($C_1$–$C_4$)-alkylene or O—($C_1$–$C_5$)-alkyl-COOR12,
wherein said ($C_1$–$C_6$)-alkyl, ($C_2$–$C_6$)-alkenyl, ($C_2$–$C_6$)-alkynyl, ($C_3$–$C_7$)-cycloalkyl, ($C_3$–$C_7$)-cycloalkyl-($C_1$–$C_4$)-alkylene and O—($C_1$–$C_5$)-alkyl-COOR12 radicals are optionally mono- or polysubstituted by F, Cl, Br, OR12, COOR12 or N(R13)(R14);

R7 is H, ($C_1$–$C_6$)-alkyl, ($C_3$–$C_7$)-cycloalkyl, ($C_3$–$C_7$)-cycloalkyl-($C_1$–$C_4$)-alkylene, ($C_2$–$C_6$)-alkenyl, ($C_2$–$C_6$)-alkynyl, ($C_1$–$C_6$)-alkylcarboxy-($C_1$–$C_6$)-alkylene, COOR12, ($C_6$–$C_{10}$)-aryl, ($C_6$–$C_{10}$)-aryl-($C_1$–$C_4$)-alkylene, heterocyclic radical, heteroaryl, heteroaryl-($C_1$–$C_4$)-alkylene or heteroarylcarbonyl,
wherein the alkyl, cycloalkyl, alkylene, alkenyl and alkynyl groups contained in said ($C_1$–$C_6$)-alkyl, ($C_3$–$C_7$)-cycloalkyl, ($C_3$–$C_7$)-cycloalkyl-($C_1$–$C_4$)-alkylene, ($C_2$–$C_6$)-alkenyl, ($C_2$–$C_6$)-alkynyl, ($C_1$–$C_6$)-alkylcarboxy-($C_1$–$C_6$)-alkylene, ($C_6$–$C_{10}$)-aryl-($C_1$–$C_4$)-alkylene and heteroaryl-($C_1$–$C_4$)-alkylene radicals are optionally mono- or polysubstituted by F, Cl, Br, OR12, COOR12, $CONH_2$, CONH($C_1$–$C_6$)-alkyl, CON[($C_1$–$C_6$)-alkyl]$_2$ or N(R13)(R14), and wherein the aryl and heteroaryl groups contained in said ($C_6$–$C_{10}$)-aryl, ($C_6$–$C_{10}$)-aryl-($C_1$–$C_4$)-alkylene, heteroaryl, heteroaryl-($C_1$–$C_4$)-alkylene and heteroarylcarbonyl radicals are optionally mono- or polysubstituted by F, Cl, Br, $NO_2$, CN, O—R12, S—R12, COOR12, N(R13)(R14) or ($C_1$–$C_6$)-alkyl;

R12 is H, ($C_1$–$C_8$)-alkyl, ($C_2$–$C_8$)-alkenyl or ($C_2$–$C_8$)-alkynyl, wherein said ($C_1$–$C_8$)-alkyl, ($C_2$–$C_8$)-alkenyl and ($C_2$–$C_8$)-alkynyl radicals are optionally mono- or polysubstituted by F, Cl, Br, OH or O—($C_1$–$C_4$)-alkyl, R13, R14 are each independently H, ($C_1$–$C_8$)-alkyl, ($C_2$–$C_g$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl,
wherein said phenyl and $SO_2$-phenyl radicals are optionally mono- or disubstituted by F, Cl, ON, OH, ($C_1$–$C_6$)-alkyl, O—($C_1$–$C_6$)-alkyl, $CF_3$, $OCF_3$, COOH, COO($C_1$–$C_6$)-alkyl or $CONH_2$; or R13 and R14, taken together with the nitrogen atom to which they are attached, form a 3–7 membered, saturated, heterocyclic ring which may contain up to 2 further heteroatoms from the group of N, O and S, and wherein said heterocyclic ring is optionally mono-, di- or trisubstituted by F, Cl, Br, OH, oxo, N(R21)(R22) or ($C_1$–$C_4$)-alkyl; and R21, R22 are each independently H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl,
wherein said phenyl and $SO_2$-phenyl radicals are optionally mono- or disubstituted by F, Cl, ON, OH, ($C_1$–$C_6$)-alkyl, O—($C_1$–$C_6$)-alkyl, $CF_3$, $OCF_3$, COOH, COO($C_1$–$C_6$)-alkyl or $CONH_2$;

with the proviso that when R5 is halogen or unsubstituted ($C_1$–$C_6$)-alkyl, R7 cannot be heterocyclic radical or heteroaryl;

with the proviso that when any of R8, R9, R10 and R11 are F, and R1 and R2 are H, and R3, R4, R5 and R6 are H, then R7 cannot be ($C_1$–$C_6$)-alkyl wherein the alkyl group is mono-substituted by COOR12 wherein R12 is H;

and pharmaceutically acceptable salts thereof.

2. The compound of claim 1 wherein

R8, R9, R10, R11 are each independently H, F, Cl, Br, OH, $NO_2$, CN or O—($C_1$–$C_6$)-alkyl,
wherein said O—($C_1$–$C_6$)-alkyl radical is optionally mono- or polysubstituted by F, Cl or Br;

R1, R2 are each H;

R3, R4, R5, R6 are each independently, H, F, Cl, Br, N02, ON, O-R12, O-phenyl, S-R12, COOR12, N(R13)(R14), ($C_1$–$C_6$)-alkyl, ($C_2$–$C_6$)-alkenyl, ($C_2$–$C_6$)-alkynyl, ($C_3$–$C_7$)-cycloalkyl, ($C_3$–$C_7$)-cycloalkyl-($C_1$–$C_{04}$)-alkylene or O—($C_1$–$C_5$)-alkyl-COOR$_{12}$,
wherein said ($C_1$–$C_6$)-alkyl, ($C_2$–$C_6$)-alkenyl, ($C_2$–$C_4$)-alkynyl, ($C_3$–$C_7$)-cycloalkyl, ($C_3$–$C_7$)-cycloalkyl-($C_1$–$C_4$)-alkylene and O—($C_1$–$C_5$)-alkyl-COOR12 radicals are optionally mono- or polysubstituted by F, Cl, Br, OR12, COOR12 or N(R13)(R14);

R7 is H, ($C_1$–$C_6$)-alkyl, ($C_3$–$C_7$)-cycloalkyl, ($C_2$–$C_6$)-alkenyl, ($C_2$–$C_6$)-alkynyl, ($C_1$–$C_6$)-alkylcarboxy-($C_1$–$C_6$)-alkylene, COOR12, ($C_6$–$C_{10}$)-aryl, ($C_6$–$C_{10}$)-aryl-($C_1$–$C_4$)-alkylene, heteroaryl, heteroaryl-($C_1$–$C_4$)-alkylene or heteroarylcarbonyl.
wherein the alkyl, cycloalkyl, alkylene, alkenyl and alkynyl groups contained in said ($C_1$–$C_6$)-alkyl, ($C_3$–$C_7$)-cycloalkyl, ($C_2$–$C_6$)-alkenyl, ($C_2$–$C_6$)-alkynyl, ($C_1$–$C_6$)-alkylcarboxy-($C_1$–$C_6$)-alkylene, ($C_6$–$C_{10}$)-aryl-($C_1$–$C_4$)-alkylene and heteroaryl-($C_1$–$C_4$)-alkylene radicals are optionally mono- or polysubstituted by F, Cl, Br, OR12, COOR12, $CONH_2$, CONH($C_1$–$C_6$)-alkyl, CON[($C_1$–$C_6$)-alkyl]$_2$ or N(R13)(R14), and wherein the aryl and heteroaryl groups contained in said ($C_6$–$C_{10}$)-aryl, ($C_6$–$C_{10}$)-aryl-($C_1$–$C_4$)-alkylene, heteroaryl, heteroaryl-($C_1$–$C_4$)-alkylene and heteroarylcarbonyl radicals are optionally mono- or polysubstituted by F, Cl, Br, $NO_2$, ON, O–R12, S—R12, COOR12, N(R13)(R14) or ($C_1$–$C_6$)-alkyl;

R12 is H, ($C_1$–$C_8$)-alkyl, ($C_2$–$C_8$)-alkenyl or ($C_2$–$C_8$)-alkynyl,
wherein said ($C_1$–$C_8$)-alkyl, ($C_2$–$C_8$)-alkenyl and ($C_2$–$C_5$)-alkynyl radicals are optionally mono- or polysubstituted by F, Cl, Br, OH or O—($C_1$–$C_4$)-alkyl;

R13, R14 are each independently H, ($C_1$–$C_8$)-alkyl, ($C_2$–$C_8$)-alkenyl, ($C_2$–$C_8$)-alkynyl, ($C_3$–$C_7$)-cycloalkyl, (C$_3$–C$_7$)-cycloalkyl-(C$_1$–C$_4$)-alkylene, COO—(C$_1$–C$_4$)-alkyl, COO—(C$_2$–C$_4$)-alkenyl, phenyl or SO$_2$-phenyl, wherein said phenyl and SO$_2$-phenyl radicals are optionally mono- or disubstituted by F, Cl, ON, OH, (C$_1$–C$_6$)-alkyl, O—(C$_1$–C$_6$)-alkyi, CF$_3$, OCF$_3$, COOH, COO(C$_1$–C$_6$)-alkyl or CONH$_2$; or R13 and R14, taken together with the nitrogen atom to which they are attached, form a 3–7 membered, saturated, heterocyclic ring which may contain up to 2 further heteroatoms from the group of N, O and S, and wherein said heterocyclic ring is optionaDy mono-, di- or trisubstituted by F, Cl, Br, OH, oxo, N(R22)(R22) or (C$_1$–C$_4$)-alkyl; and R21, R22 are each independently H or (C$_1$–C$_8$)-alkyl.

3. The compound of claim 2 wherein

R8, R9, R10, R11 are each independently H, F or Cl;

R1, R2, R4, R6 are each H;

R3, R5 are each independently H, Cl, OR12, COOR$_{12}$, N(R13)(R14) or (C$_1$–C$_6$)-alkyl;

R7 is (C$_1$–C$_6$)-alkyl, wherein said (C$_1$–C$_6$)-alkyl radical is optionally mono- or polysubstituted by F, OR12, COOR$_{12}$ or N(R13)(R14), (C$_3$–C$_6$)-cycloalkyl, (C$_2$–C$_6$)-alkenyl, (C$_2$–C$_6$)-alkynyl, (C$_1$–C$_5$)-alkylcarboxy-(C$_1$–C$_6$)-alkylene, COOR12, phenyl, wherein said phenyl radical is optionally mono- or polysubstituted by F, OMe or OCF$_3$, or benzyl, wherein the phenyl ring of said benzyl radical is optionally substituted by OMe, pyridyl, thienyl, furanyl, indolylcarbonyl or benzofuranyl, wherein said benzofuranyl radical is optionally substituted by Cl or OMe;

R12 is H or (C$_1$–C$_8$)-alkyl, wherein said (C$_1$–C$_8$)-alkyl radical is optionally mono- or polysubstituted by F;

R13, R14 are each independently H or (C$_1$–C$_8$)-alkyl; or

R13 and R14, taken together with the nitrogen atom to which they are attached, form a 5-membered, saturated heterocyclic ring.

4. A pharmaceutical composition comprising a compound of claim 1 and a pharmaceutically acceptable carrier.

5. The pharmaceutical composition of claim 4 further comprising one or more blood sugar-reducing active ingredients.

6. The pharmaceutical composition of claim 4 further comprising one or more statins.

7. A method of treating type 2 diabetes comprising administering to a patient in need thereof a therapeutically effective amount of a compound of claim 1.

8. A method for lowering blood sugar comprising administering to a patient in need thereof a therapeutically effective amount of a compound of claim 1.

9. A method of treating type 2 diabetes comprising administering to a patient in need thereof a therapeutically effective amount of a compound of claim 1 in combination with at least one further blood sugar-reducing active ingredient.

10. A method for lowering blood sugar comprising administering to a patient in need thereof a therapeutically effective amount of a compound of claim 1 in combination with at least one further blood sugar-reducing active ingredient.

* * * * *